United States Patent
Zhang et al.

(10) Patent No.: US 8,986,191 B2
(45) Date of Patent: Mar. 24, 2015

(54) DISPOSABLE DEVICE FOR VAGINAL CLEANING AND HYGIENE

(76) Inventors: Zhengping Zhang, Sterling, VA (US); Liang Zhang, New Haven, CT (US)

(*) Notice: Subject to any disclaimer, the term of this patent is extended or adjusted under 35 U.S.C. 154(b) by 2399 days.

(21) Appl. No.: 11/819,518

(22) Filed: Jun. 28, 2007

(65) Prior Publication Data

US 2009/0005635 A1 Jan. 1, 2009

(51) Int. Cl.
*A61F 5/00* (2006.01)
*A61M 3/02* (2006.01)
*A61H 19/00* (2006.01)
*A61H 23/02* (2006.01)
*A61M 31/00* (2006.01)

(52) U.S. Cl.
CPC ............ *A61M 3/0279* (2013.01); *A61H 19/44* (2013.01); *A61H 19/50* (2013.01); *A61H 23/0263* (2013.01); *A61M 31/00* (2013.01); *A61H 2201/0103* (2013.01); *A61H 2201/5097* (2013.01); *A61M 2205/05* (2013.01); *A61H 2201/105* (2013.01); *A61H 2201/1688* (2013.01)
USPC ........................................... 600/38; 604/279

(58) Field of Classification Search
USPC ........ 600/38–41; 604/1, 35, 83, 84, 212, 279; 601/67, 68, 80
See application file for complete search history.

(56) References Cited

U.S. PATENT DOCUMENTS

| | | | |
|---|---|---|---|
| 797,676 A * | 8/1905 | Flowers | 604/103.01 |
| 3,495,589 A | 2/1970 | Clement | |
| 3,598,106 A * | 8/1971 | Buning | 600/591 |
| 3,690,319 A * | 9/1972 | Marco et al. | 604/106 |
| 4,281,648 A | 8/1981 | Rogers | |
| 5,045,058 A | 9/1991 | Demetrakopoulos | |
| 5,333,621 A * | 8/1994 | Denzer | 128/844 |
| 5,573,499 A * | 11/1996 | McAllister | 601/70 |
| 5,823,939 A | 10/1998 | Tsagarakis | |
| 5,944,734 A * | 8/1999 | Hermann et al. | 606/192 |
| 6,280,403 B1 * | 8/2001 | Lok | 601/70 |
| 6,578,205 B1 | 6/2003 | King | |
| 6,599,236 B1 | 7/2003 | Castro | |
| 6,749,557 B2 * | 6/2004 | Garland | 600/38 |

* cited by examiner

*Primary Examiner* — Samuel Gilbert

(57) ABSTRACT

A disposable device (10, 11, 12, 13, 14, 15, 16, 17 or 18) both for vaginal cleaning and hygiene and for sexual aid and its methods of use are disclosed. The device comprises a pouch or bladder (30 or 30') with an open-end or opening (34 or 34') and in substantial shape and size of the condom and a standard valve (20 or 20') or closure (20") with a base (22, 22' or 22"). The pouch or bladder is made of a layer of flexible and inelastic airtight durable material. The opening is fluid-tightly sealed to the base or by the cap (24") and neck of the closure. The inflated or filled device functions as dildos and, when enclosing a mini-vibrator, as vibrators. The poked device is used for delivering medication to appropriate areas of the vagina and for washing the vagina with water. The pouch or bladder is packed in a small sealed package before use and is disposable after use.

12 Claims, 3 Drawing Sheets

DISPOSABLE DEVICE FOR VAGINAL CLEANING AND HYGIENE

CROSS-REFERENCE TO RELATED APPLICATIONS

Not Applicable

FEDERALLY SPONSORED RESEARCH

Not Applicable

BACKGROUND OF THE INVENTION

1. Field of Invention

This invention relates to disposable and inflatable devices for the cleansing and antisepsis of the vagina and for sexual aid.

2. Prior Art

For self-treatments of vaginal irritation, itching or infections and regular hygiene of the vagina, difficulties usually arise because the inner end of the vagina is ring-shaped, with the vaginal dome collapsing against the uterine cervix (anterior and posterior fornix). In addition, the vaginal walls are normally collapsed against each other; and the inner surfaces of the vaginal walls have multiple rugae, villi, folds and creases. U.S. Pat. No. 5,045,058 to Demetrakopoulos disclosed a phallic-shaped apparatus for the cleansing and antisepsis of the vagina that has some advantages over standard douching techniques. The apparatus with a phallic-shaped solid soap body can overcome the limitations of douching simply because the user can stretch the vagina walls and can even sequentially stretch particular parts of the vagina while at the same time applying soap and medication to these parts. The apparatus can deliver the lather formed on the outer surface of the phallic-shaped body to appropriate areas of the vagina. This stretching of the vagina may also allow for the draining of undesirable vaginal secretions from between inflamed rugae or folds. Therefore, it is the phallic or dildo-like shape that makes the apparatus efficient and effective at disinfecting the vagina, particularly when medicated solutions are used. Unfortunately, the reusable feature of the apparatus itself may cause some health concerns.

In a very different field, dildos have been commonly used for sexual aid by stimulation of erogenous zones of the human body. Examples include the use of dildos for insertion into body orifices such as the vagina. The development of modern plastics and other moldable materials has enabled the mass production of dildos in a wide variety of forms in shape, design texture and size. Dildos can be as simple as solid smooth-edged/contoured cylinders or as complex as replicas of human penises. Because of the material costs, dildos are mostly designed for reuse. However, even if people are willing to spend time and money, it is still burdensome to clean or sterilize dildos thoroughly after use to avoid any health concerns. Many dildos, mostly made of less expensive materials, cannot be sterilized via boiling or washing with detergents.

Although people have accepted sexual aid devices such as dildos or vibrators for enhancing sexual pleasure, most people want to keep sexual devices concealed when not in use for fear of embarrassment. Therefore online sales of sexual devices become popular and more dominant than sex shops. However, it is very difficult to conceal dildos in marketing, selling, purchasing, and storing because of their solid materials and considerable shapes and sizes. Thus some dildos are made at small sizes but they have compromised effectiveness; others are made in shapes of regular toys or products but they waste extra materials and time. There are some thick-shelled rubber dildos with integral hand pumps, available in the current market, called "inflatable dildos" with the capacity of increasing lateral size with air. However, just like other dildos, they are not flexible and cannot be packed into a small package because of their full longitudinal sizes and considerable lateral sizes. All these limit or suppress the marketing power, distribution capacity and market supply of dildos since no major retail stores in the United States sells dildos in any current forms.

Therefore, it would be very desirable to have a simple device 1) that can be used for the cleansing and antisepsis of the vagina; 2) that can function fully as a dildo of any predetermined size; 3) that has a flexibility to be packed in a small sealed package, substantially like a condom; 4) that is light for shipping and handling, convenient to carrying or storing, and easy to use; and 5) that is cheap enough to be disposable after one-time use. Thus, such a device would be more acceptable to the public, more marketable, and more suitable to be sold not only through the Internet or mail order but also in pharmacies and retail stores.

Accordingly, it is an object of the present invention to provide such a device that has all these advantages described above. Further objects and advantages will become apparent from a consideration of the ensuing description and drawings.

SUMMARY OF THE INVENTION

This invention presents a disposable device both for vaginal cleaning and hygiene and for sexual aid and methods of use thereof.

In accordance with several embodiments, the disposable device comprises a bladder that is shaped substantially as a smooth-contoured cylinder at one end, like an ordinary condom without the nipple-end, and made of a thin layer of flexible, inelastic, airtight and durable material. The bladder has an opening that can be fluid-tightly sealed by a standard valve or closure or the like at the other end. The bladder can be inflated or filled by fluid through the valve or closure or the like. When inflated or filled, the bladder can penetrate the vagina as a dildo. The bladder can be packed and sealed into a small package when empty. Such a bladder can be easily molded or textured in a variety of shapes, designs, colors or sizes. It can be coated permanently with a layer of materials, such as flexible absorbent material or an elastomeric gel that has the general tactile feel of human flesh. It can also have a temporary coating of materials, such as lubricant agent or liquid detergent.

For use, the device is first inflated or filled, either by blowing or by pouring water in, through the valve or closure or the like. When used as sexual aid, it can be either pre-lubricated or lubricated if desired. The method of use of the inflated or filled device is the same as that of ordinary dildos. When enclosing a mini-vibrator, the device functions as a conventional vibrator. For vaginal cleaning and hygiene, the device's method of use may depend on the physical forms of substances or medicines used. Medication or antiseptics in cream or gel are preferably applied onto the surface of the inflated or filled device before the device is inserted into the vagina. However, medication or antiseptics in liquid or solution are preferably, with water or alone, filled into the chamber of the device when inflating. After poking a few small holes in its walls with a sharp object such as a pinhead, the user inserts the device into the vagina and moves it to the appropriate areas. The medicine is delivered through the holes under the internal fluid pressure. When finished or deflated, the device is withdrawn from the vagina. The device can be refilled and inserted into the vagina repeatedly if desired. Similarly, the poked device can be also utilized for washing the vagina with detergent and water. After use, the device or only the bladder may be disposed.

DRAWINGS—FIGURES

DETAILED DESCRIPTION—PREFERRED EMBODIMENTS—FIGS. 1-5

Figure 1:
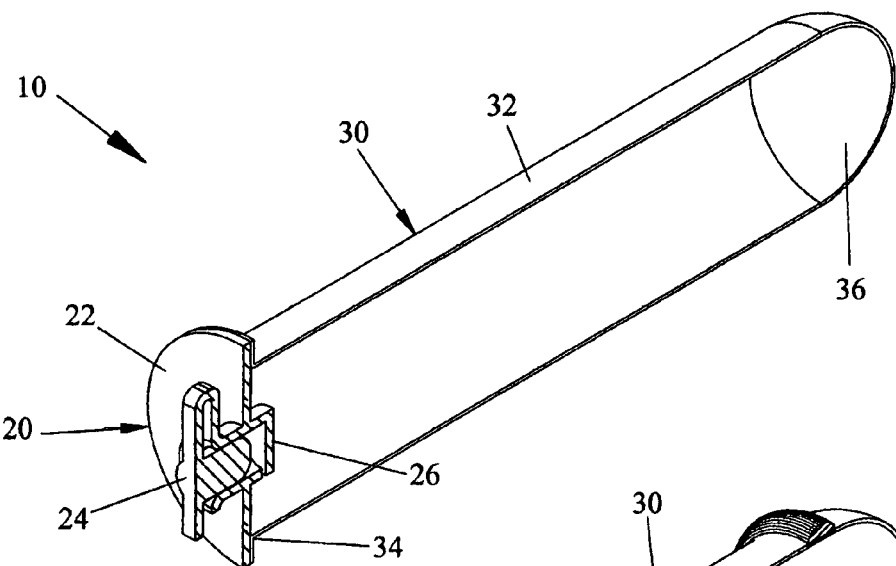
FIG. 1 is a perspective sectional view of an inflated or filled device in accordance with one embodiment of the present invention.

Device 10, a preferred embodiment of the present invention, is illustrated in FIG. 1. The device comprises a standard valve 20, as well known in the art, and an airtight bladder, sheath or pouch 30 that is in shape of phallic cylinders or condoms and is made of a sheet of flexible, inelastic, and durable material, such as PVC. The pouch comprises a cylindrical body 32, an opening or open-end 34 and a rounded head or close-end 36. The open-end is connected, sealed and/or welded air-tightly with a seat or base 22 of valve 20 at their peripheries. The chamber of pouch 30 is in fluid communication with the environment only through valve 20 and, when fully stretched, is substantially of size of the penis. A plug 24 and flap 26 of the valve can close the opening or tube of the valve.

Figure 2:
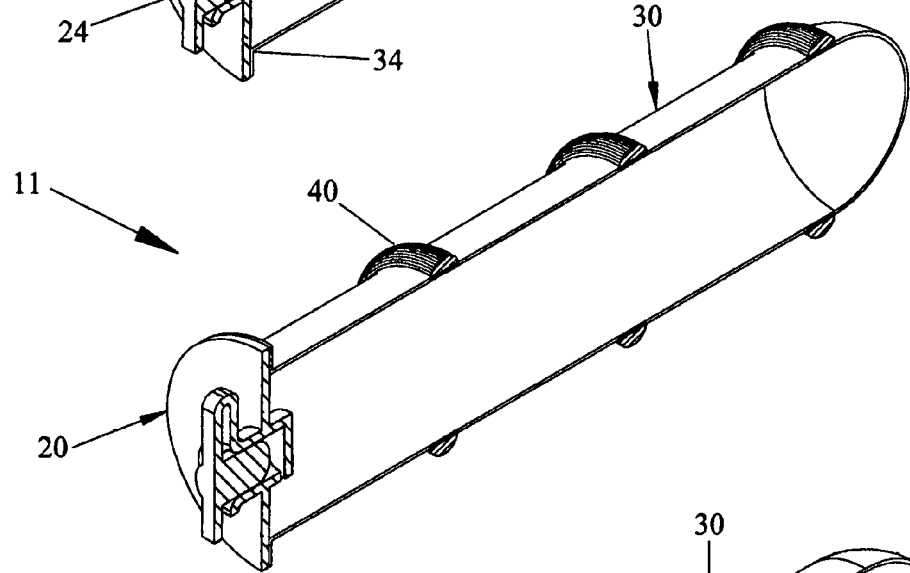
FIG. 2 is a perspective sectional view of an inflated or filled device with ring textures in accordance with another embodiment of the present invention.

Device 11, an alternative embodiment to the preferred embodiment, is illustrated in FIG. 2. The device comprises the same components and configurations as those of device 10 except that the surface of body 32 is textured with rings 40. A plurality of rings 40 are spaced substantially equidistantly along the length of the body and molded on or fastened onto the outer surface of the body. Ring 40 is preferably made of solid material. The ring texture is only one of a wide variety of textures that can be textured on the surface.

Figure 3:
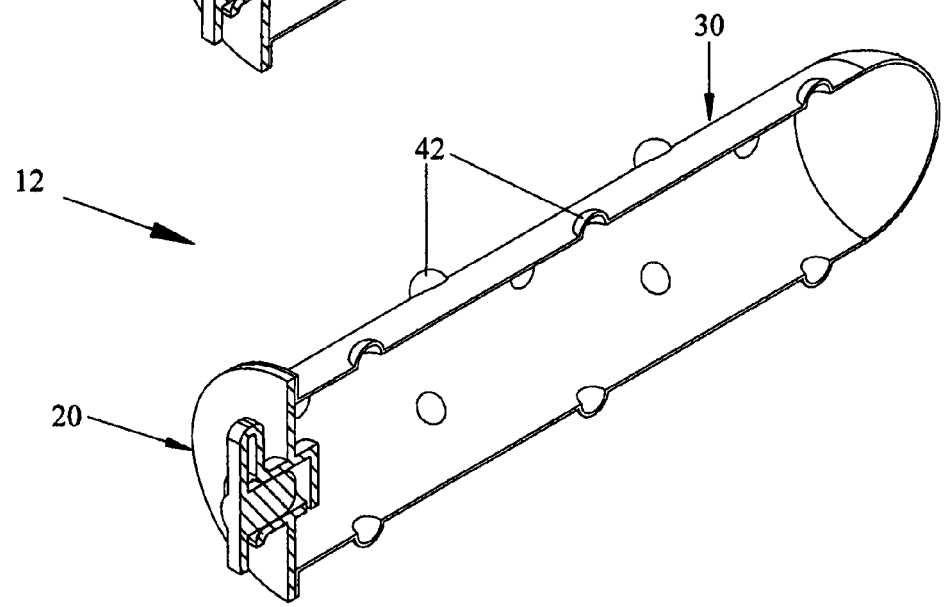
FIG. 3 is a perspective sectional view of an inflated or filled device with a bubble surface in accordance with another embodiment of the present invention.

Device 12, another alternative embodiment to the preferred embodiment, is illustrated in FIG. 3. The device comprises the same components and configurations as those of device 10 except that body 32 has a spotty surface with bubbles 42, instead of a smooth one. Body 32 is molded so that bubbles 42 are hollow and only in fluid communication with the main chamber of pouch 30. The bubble spot is only one of a variety of the hollow posts that can be molded with body 32 on the surface.

Figure 4:
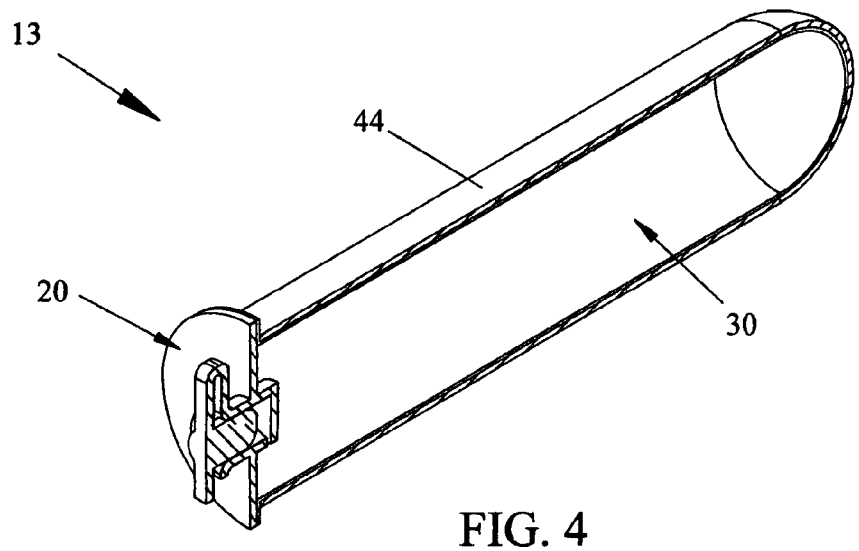
FIG. 4 is a perspective sectional view of an inflated or filled device with a coating in accordance with another embodiment of the present invention.

Device 13, another alternative embodiment to the preferred embodiment, is illustrated in FIG. 4. The device comprises the same components and configurations as those of device 10 except for an additional coat or coating 44 on the surface of pouch 30. Coating 44 is a layer of liquid or solid flexible material and is mounted onto or bonded with the surface of pouch 30 either temporarily or permanently. As well known in the art, coating is an economic and efficient way to improve the physical and chemical properties of the surface of pouch 30. A coat of flexible absorbent material can increase the liquid absorbability of the device; a coat of an elastomeric gel may provide the general tactile feel of human flesh; a coat of latex may provide further hygiene; and a temporary coating of lubricant agent can reduce the friction of the device with the human skin.

Figure 5:
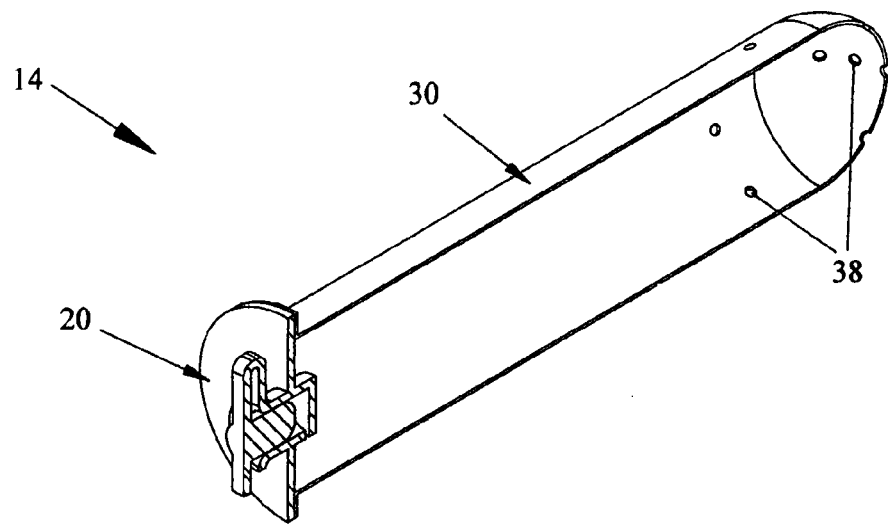
FIG. 5 is a perspective sectional view of an inflated or filled device with small holes in accordance with another embodiment of the present invention.
Figure 6:
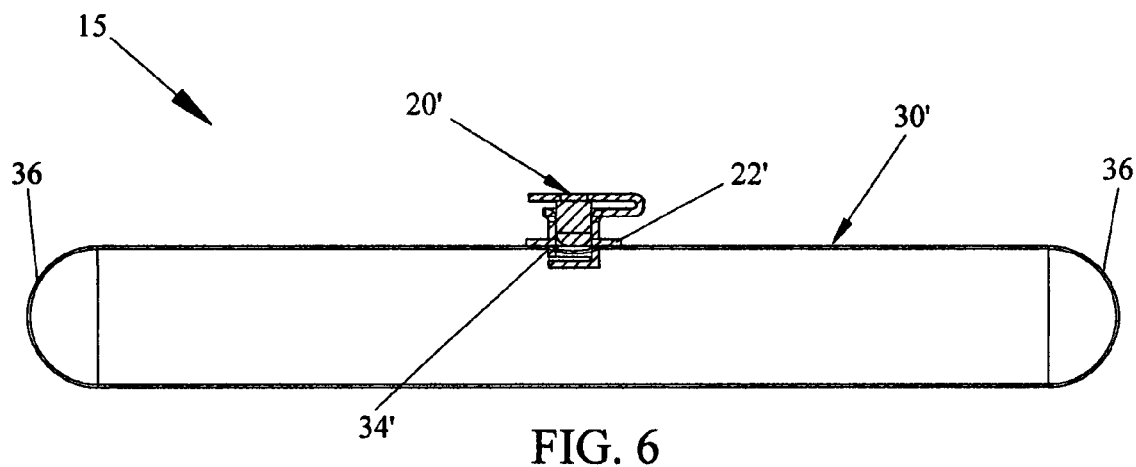
FIG. 6 is a sectional view of an inflated or filled device with double rounded ends in accordance with another embodiment of the present invention.

Device 14, another alternative embodiment to the preferred embodiment, is illustrated in FIG. 5. The device comprises the same components and configurations as those of device 10 except that pouch 30 has a plurality of small holes 38 in its walls. The holes are preferably made in or near head 36. Fluid inside the pouch can escape through the holes slowly or quickly, depending on the size and number of the holes. Holes 38 can be made by manufacturers or by users poking the walls of pouch 30 with a needle or pinhead. Similarly, the holes can also be made to devices 11, 12, and 13.

Operation—Preferred Embodiments—FIGS. 1-5

The flexibility of pouch 30 allows emptied or deflated devices 10, 11, 12, 13, and 14 to be packed into a small package (not shown). Such a package may be sealed in ways well known in the art for hygiene, convenience and concealing. The package can be torn open or pulled apart at its bonded seams, as known in the art.

After removed from the package, device 10, 11, 12, or 13 is inflated by air or filled by water/liquid. The user loads the device either by blowing or by filling water/liquid in through valve 20. The water/liquid is preferably warmed before the fill. The user can lubricate the surface of pouch 30 if desired and if it is not pre-lubricated. Thus, the device can be ready for use as a full sized dildo. The tactile sensation is enhanced by textures 40 of device 11 or by filled bubbles 42 of device 12. Furthermore, the use of the device as dildo may relax the muscle of vagina first so that the device with medication can be easily inserted into the vagina for the application of a medicine or antiseptic thereafter.

Figure 9:
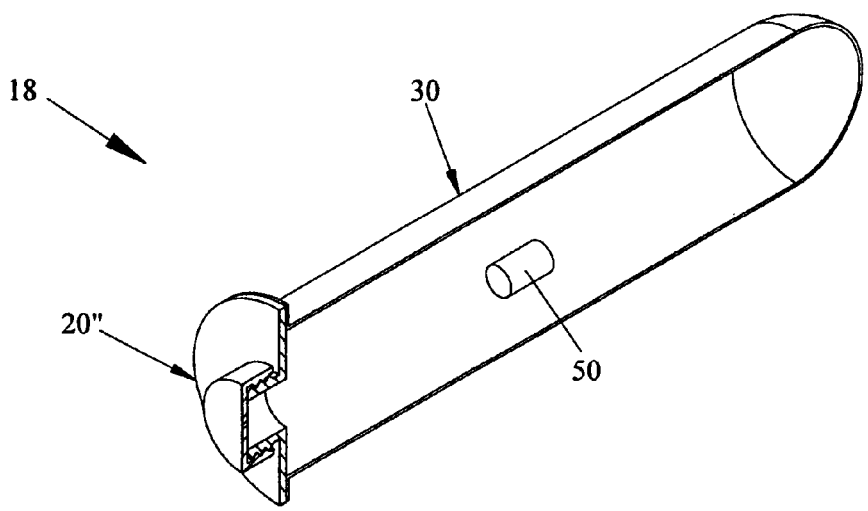
FIG. 9 is a perspective sectional view of a liquid-filled device enclosing a mini-vibrator in accordance with another embodiment of the present invention.

Device 10, 11, 12, or 13 can be an alternative to or replacement of a vibrator for enhancing sexual pleasure if the device encloses a mini-vibrator in the chamber of pouch 30, not shown here but similarly illustrated in FIG. 9 for mini-vibrator 50 in device 18. The make and use of mini-vibrators are known in the art. For mini-vibrators with a wireless or remote control, such a mini-vibrator may be pre-enclosed in the device when manufactured and the cord for a remote control, if any, may be pre-installed through base 22. After inflating or filling the device, the user starts the vibration. The mini-vibrator should also be waterproof or functional in water if the device intends to be filled with water. For mini-vibrators without wireless or remote controls, the user starts a mini-vibrator before inserting it into the device. This operation can be performed before or after filling the device with water. However, if the device is inflated with air, the operation should be done before inflating. If the check flap 26 of valve 20 is too much of an obstacle against the insertion of the mini-vibrator, valves with different designs or mechanisms (not shown) should be used instead. It is known in the art that the tube and the check flap of some valves are separable or detachable before closing. Such valves can provide wider openings for the insertion of the mini-vibrator. The mini-vibrator may be recharged and reused.

For the cleansing and antisepsis of the vagina, the user first applies a layer of the medicine or antiseptic on the surface of pouch 30 of device 10, 11, 12, or 13 if the substance, in a physical form such as cream, can be temporally coated on the surface. Then the user inserts the device into the vagina, moves it to appropriate areas of the vagina and withdraws it from the vagina when finishing. This procedure is repeated until sufficient substance has been delivered to the needed areas.

Device 13 with coating 44 of absorbent material can absorb liquid medicines or antiseptics well and, then, can be used in a similar procedure to that described above.

Furthermore, the user can fill medicines or antiseptics in liquid or solution, mixed with water or alone, into device 10, 11, 12, or 13 when loading it. After poking a few small holes 38, preferably on the area near head 36, in the walls of pouch 30 with a fine sharp object such as a pinhead the user inserts the device (like device 14) into the vagina and moves it to the appropriate areas. The substance (medicine or antiseptic) is delivered through holes 38 under the internal fluid pressure. The user may squeeze the device to accelerate the deliver process. When finished or discharged, the device is withdrawn from the vagina. Holes 38 are small in size so that the discharge process of the device through the holes is slow enough to allow the device to be refilled and inserted into the vagina repeatedly. A pre-holed device 14 can be utilized in the same manner as described for the cleansing and antisepsis of the vagina.

Furthermore, the poked device 10, 11, 12, or 13 or pre-holed device 14 can be also utilized for washing the vagina with detergent liquid or water in the same way as described above. This procedure can be repeated until the vagina has been adequately flushed.

After use, the device may be disposed to further avoid any potential for sexually transmitted diseases or other health concerns.

DETAILED DESCRIPTION AND OPERATION

—Alternative Embodiments—FIGS. 6-9

Device 15, an alternative embodiment to the preferred embodiments of the present invention as described above, is illustrated in FIG. 6. The device comprises a standard valve 20', a bladder 30' in the shape of a cylinder with two rounded-ends and made of a sheet of flexible and inelastic durable airtight material, and an opening 34' in the wall of the bladder. Valve 20' is almost identical to valve 20 except that the former has a base 22' significantly smaller than base 22 of the latter. Bladder 30' can be also formed with two pouches 30 that are air-tightly and smoothly connected at the peripheries of their open-ends 34. Opening 34' is preferably located at the substantial middle of bladder 30' and is air-tightly sealed with base 22' at their peripheries. The chamber of bladder 30' is in fluid communication with the environment only through valve 20'. Similar to devices 10, 11, 12, and 13, device 15 can be loaded by air or liquid and used as a dildo with double heads.

Figure 7:
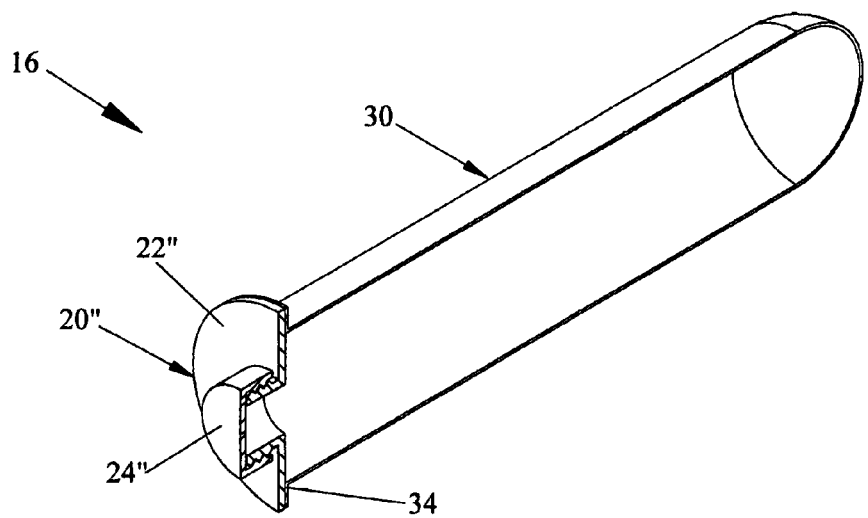
FIG. 7 is a perspective sectional view of a liquid-filled device in accordance with another embodiment of the present invention.
Figure 8:
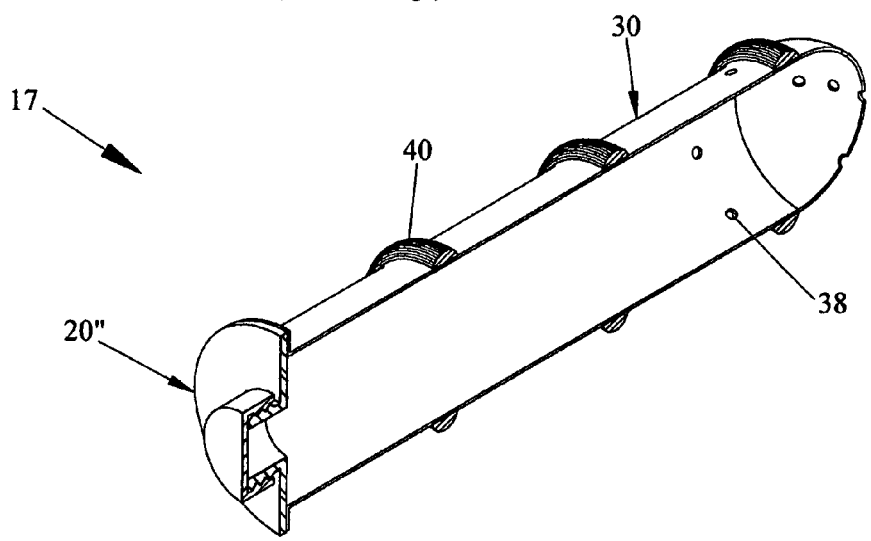
FIG. 8 is a perspective sectional view of a liquid-filled device with ring textures and small holes in accordance with another embodiment of the present invention.

Device 16, another alternative embodiment to the preferred embodiments of the present invention, is illustrated in FIG. 7. The device is almost the same as device 10 except that valve 20 is replaced by a bottle's mouth/neck and cap structure 20''' that is known in the art. A shoulder or base 22'', similar to base 22, connects the neck and seals open-end 34 of pouch 30 fluid-tightly. Alternatively, when the pouch substantially conforms to the inner surface of the neck (not shown), the open-end is mounted, by its bead or rim and through the neck, on the top of the neck or the mouth. The cap 24'' can be screwed and secured onto the neck and can seal the mouth, therefore the pouch, fluid-tightly. Device 16 is easy to use with liquid. A user simply removes cap 24'' from the mouth, fills the device with preferably warm or warmed water or liquid through the mouth or open-end 34, and screws the cap on again. The filled device 16 can be used as a dildo or a tool for the cleansing and antisepsis of the vagina, similar to devices 10, 11, 12, and 13. The body of device 16 or pouch 30 can be also textured or molded as shown with devices 11 or 12. FIG. 8 illustrates device 17—textured device 16 with a plurality of rings 40 and poked or pre-holed. After use, device 16 or 17 is disassembled and the whole device or only the pouch is disposed.

Device 18—device 16 enclosing a mini-vibrator 50 is illustrated in FIG. 9. Mini-vibrator 50 is either waterproof or functional in water. Furthermore, the mini-vibrator is preferably wirelessly or remotely controllable. Its control can be built in or integrated with cap 24''. Before use, mini-vibrator 50 is usually kept separately from device 16 or pouch 30. A user puts the mini-vibrator into the chamber of device 16 before or after filling the device with water. The filled device 16 containing the mini-vibrator —device 18 functions as a vibrator for sexual aid. Furthermore, device 18 can be easily assembled or disassembled so that the mini-vibrator can be recharged and reused, but the rest or the pouch is disposable.

CONCLUSION, RAMIFICATIONS, AND SCOPE

Accordingly the reader can see that, according to the various embodiments of the present invention, we have provided a disposable device for the cleansing and antisepsis of the vagina and for sexual aid.

A number of advantages of the present invention, from the descriptions above, is evident:

It is a simple, safe, effective and economical (or low cost) device.

It can be effectively used for the cleansing and antisepsis of the vagina.

It is cheap enough to be disposable after one-time use for avoiding any health concerns.

It can be easily packed in a small sealed package and concealed in marketing, selling, purchasing, and storing.

It is a simple, cheap, effective and safe alternative to or replacement of vibrators for sexual pleasure when enclosing a micro-vibrator.

It significantly reduces the amount of materials needed for conventional dildos while it still functions fully as a dildo with any size, feel and comfort.

It is light, allowing for easy and convenient carrying, shipping and handling.

It easily enhances comfort of use by filling with warm water.

It can be easily manufactured in a variety of shapes, sizes, textures and colors.

It is suitable for sale not only through the Internet or mail order but also in pharmacies and retail stores as healthcare products.

Therefore, the embodiments of the invention are more acceptable for the public, demandable, and marketable than similar products currently sold.

While the above description contains many specificities, they should not be construed as limitations on the scope of the invention, but as exemplifications of the presently preferred embodiments thereof. Many other ramifications and variations are possible within the teachings of the inventions. For example, 1) there can be different combinations of the embodiments described above, such as that the embodiments with the cap can also be air-inflatable if the cap is integrated with a valve; 2) the body of the device can be made in a wide variety of shapes, sizes, textures and colors; 3) the device can use a variety of different valves and closures in design or mechanism; and 4) the configuration of the device can be very different from what is illustrated in the embodiments described above, such as that the open-end of the pouch can be sealed to the base on its top, instead of on its bottom, or to the top of the neck or the mouth.

Thus the scope of the invention should be determined not by the embodiments illustrated, But by the appended claims and their legal equivalents.

We claim:

1. A collapsible device for vaginal cleaning and hygiene and for sexual aid, comprising:
   (a) a substantially phallic-shaped pouch with a smooth-contoured close-end made of a sheet of substantially flexible and inelastic fluid-impervious material, and
   (b) a closure means for sealing fluid-imperviously the open-end of said pouch including a check valve that enables a user to inflate said pouch by mouth or a combination of a bottle-neck and a bottle-closure, thereby said pouch can be inflated or filled by fluid and be deflated or emptied through said closure means,
      whereby said device can be collapsed, packed and sealed in a small package when empty, can penetrate the vagina as a dildo when inflated or filled, and can deliver a medicine or antiseptic thereon to appropriate areas of the vagina.

2. The device of claim 1, further including:
   (c) a plurality of apertures in said pouch,
      whereby said device can be used, when filled up with detergent liquid or water, for washing the vagina or, when filled up with liquid medication, for the cleansing and hygiene of the vagina.

3. The device of claim 1 wherein said pouch is coated, textured or molded,
   whereby said device can have different shapes and surfaces.

4. The device of claim 1 wherein said pouch is detachable or separable from said closure means,
   whereby said pouch alone is disposable, replaceable, and concealable.

5. A collapsible device for vaginal cleaning and hygiene and for sexual aid, comprising:
   (a) a substantially phallic-shaped pouch with a smooth-contoured close-end made of a sheet of substantially flexible and inelastic fluid-impervious material,
   (b) a closure means for sealing fluid-imperviously the open-end of said pouch including a check valve that enables a user to inflate said pouch by mouth or a combination of a bottle-neck and a bottle-closure, thereby said pouch can be inflated or filled by fluid and be deflated or emptied through said closure means, and
   (c) a mini-vibrator enclosed inside said pouch,
      whereby said device can function as a vibrator for sexual pleasure when inflated or filled, can be collapsed, packed and sealed in a small package when empty, can penetrate the vagina as a dildo when inflated or filled, and can deliver a medicine or antiseptic thereon to appropriate areas of the vagina.

6. The device of claim 5 wherein said mini-vibrator is wirelessly or remotely controllable.

7. A collapsible device for vaginal cleaning and hygiene and for sexual aid, comprising:
   (a) an elongated fluid-impervious bladder substantially of lateral size of the penis having a closure means for inflating or filling and at least a smooth-contoured end, wherein said closure means includes a check valve that enables a user to inflate said pouch by mouth or a combination of a bottle-neck and a bottle-closure and said bladder is made of a thin layer of flexible and substantially inelastic material and is inflated, filled, or emptied through said closure means.

8. The device of claim 7, further including:
   (b) a mini-vibrator with a wireless or remote control enclosed inside said bladder.

9. The device of claim 7 wherein said bladder is coated with a layer of flexible absorbent material,
   whereby said device can be used to absorb medication in liquid and, after inflated or filled, to deliver said medication to appropriate areas of the vagina.

10. The device of claim 7 wherein said bladder is coated, textured, or molded,
    whereby said device can have different contours and surfaces.

11. The device of claim 7 wherein said closure means is detachable or separable from said bladder partially or completely,
    whereby said closure means is at least partially reusable.

12. The device of claim 11 wherein said closure means is integrated with a mini-vibrator, a control thereof, or a power unit thereof.

* * * * *